(12) United States Patent
Kaufmann et al.

(10) Patent No.: US 7,569,339 B2
(45) Date of Patent: Aug. 4, 2009

(54) USE OF FLOW-CYTROMETRIC ANALYSIS TO OPTIMIZE CELL BANKING STRATEGIES FOR CHO CELLS

(75) Inventors: Hitto Kaufmann, Ulm (DE); Juergen Fieder, Unterstadion (DE); Ralf Otto, Oggelshausen (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 78 days.

(21) Appl. No.: 11/270,236

(22) Filed: Nov. 9, 2005

(65) Prior Publication Data

US 2006/0121444 A1    Jun. 8, 2006

(30) Foreign Application Priority Data

Nov. 10, 2004    (EP) ................... 04026673

(51) Int. Cl.
*C12Q 1/00*    (2006.01)
*G01N 33/48*    (2006.01)
*C12N 5/02*    (2006.01)

(52) U.S. Cl. .................. 435/4; 435/40.5; 435/325; 435/358

(58) Field of Classification Search .......... 435/4, 435/40.5, 325, 358
See application file for complete search history.

(56) References Cited

FOREIGN PATENT DOCUMENTS

WO    WO2006/051065 A3    5/2006

OTHER PUBLICATIONS

Sion et al., Int J Androl., Apr. 2004, 27(2):108-114.*
Yun et al., J of Bioscience and Bioeng, 2001, vol. 91, No. 6, 581-585.*
Lund, P.K., et al; Flow Cytometric Evaluation of Apoptosis, Necrosis and Recovery Wwhen Culturing Monocytes, Journal of Immunological Methods, Jun. 1, 2001, Netherlands, vol. 252, pp. 45-55.
Yael Gavrieli, et al; Identification of Programmed Cell Death In Situ Via Specific Labeling of Nuclear DNA Fragmentation; The Journal of Cell Biology (1992) vol. 119, No. 3, pp. 493-501.
J. Groth, et al; Freezing of Cells—Replacement of Serum by Oxypolygelatine; Journal of Immunological Methods (1991) vol. 141, pp. 105-109.
David L. Vaux, et al; Cell Death in Development; Cell (1999) vol. 96, pp. 245-254.
O. W. Merten; Safety Issues of Animal Products Used in Serum-Free Media; Dev. Biol Stand. (1999) vol. 99, pp. 167-180.
David P. Steensma, et al; Flow Cytometric Methods for Detection and Quantification of Apoptosis; Methods in Molecular Medicine (2003) vol. 85, pp. 323-332.
International Search Report for PCT/EP2005/055784 mailed Jun. 6, 2006.

* cited by examiner

*Primary Examiner*—Ruth A Davis
(74) *Attorney, Agent, or Firm*—Michael P. Morris; David L. Kershner; Mary-Ellen M. Devlin (57) ABSTRACT

Production of biopharmaceuticals from CHO cells requires generation of master-, working- and post-production cell banks of high quality, partly under GMP conditions. An optimal cryopreservation strategy is needed for each new production cell line, particularly with regard to the desire to establish production processes that are completely devoid of serum or even any animal components and to ensure robust thaw performance for reliable production. Here we describe a novel strategy employing flow cytometric (FC) analysis of Annexin V-stained cells for high-throughput characterization of CHO cell banks. Our data show that this method enables evaluation of a cryopreservation procedure just 6 h after thaw.

5 Claims, 4 Drawing Sheets

4 weeks old Medium
Apoptosis: 67%
Viability: 89% (hem.cyt.)

G1: 42,9
S: 47,4
M: 9,7

4 weeks old Medium
+ spike of fresh essential medium compound
Apoptosis: 42%
Viability: 91% (hem.cyt.)

G1: 43,3
S: 43,2
M: 13,5

Freshly prepared Medium
Apoptosis: 35%
Viability: 93% (hem.cyt.)

USE OF FLOW-CYTROMETRIC ANALYSIS TO OPTIMIZE CELL BANKING STRATEGIES FOR CHO CELLS

BACKGROUND OF THE INVENTION

1. Field of the Invention

The present invention relates to the production of biopharmaceuticals in CHO cells. Particularly, it pertains to the generation of master-, working- and post-production cell banks of high quality via cryopreservation. More particularly, it pertains to the propagation and characterization of cells cryopreserved in master-, working- and post-production cell banks. Furthermore, the present invention refers to a novel strategy employing flow cytometric (FC) analysis of Annexin V-stained cells for high-throughput characterization of cryopreserved cell banks.

2. Background of the Invention

The market for biopharmaceuticals for use in human therapy continues to grow at a very high rate in the last decade. CHO cell lines are one of the most attractive mammalian expression system for production, safety, and regulatory aspects. To ensure therapeutic products of uniform quality, the cell banking system of these cell lines is crucial. Creation of Master Cell Banks (MCB), Working Cell Banks (WCB), and Post Production Cell Banks (PPCB) of CHO cells are essential steps in development of production processes for biopharmaceuticals in that cell lines. The quality of these banks is critical, as their generation not only supports clinical development of the product but also ultimately the market supply phase.

The main parameter that characterizes the quality of a cell bank is the long term survival of cultured cells after thawing. Moreover, besides the long term survival, robustness and stability are also essential properties of a suitable cell bank. The time it takes from thawing a vial to establishing inoculum cultures of robust growth, genetic stability and high culture viability is critical for assessing the quality of a cell bank. Finally, a cell bank of high quality should guarantee for all of these parameters to remain stable over a prolonged storage period of the bank. All these characteristics highly depend on the method of cryopreservation for a given production cell line.

Today, an increasing number of biopharmaceuticals is produced from CHO cells due to their ability to correctly process and modify human proteins. The first generation of CHO cell-based production processes almost exclusively required the presence of serum in the culture medium. Safety and regulatory benefits led to development of new cell lines and culture regimes that now enable serum-free cultivation of cells throughout the process (Merten, 1999). However, the removal of serum from the entire production process also requires cells to be stored in master and working cell banks with serum-free freezing media. A variety of strategies have been described for cell banking of cells by using cryoprotectants that are able to at least partially replace the protective effects of serum (Groth et al., 1991). However, the success of any such strategy highly depends on the cell line, the medium, and the protocol for freezing and thawing. Therefore, evaluation of different cryopreservation strategies is essential for successful process development.

Currently, the first assessment of a newly generated cell bank is performed by thawing a defined number of vials and culturing cells for 5-10 passages. Cell number and viability as determined by trypan blue exclusion are the routinely used parameters to describe the recovery of cells after cryopreservation.

Programmed cell death or apoptosis is a process crucial for proper embryonic development and tissue homeostasis in the adult. Programmed cell death is controlled by a specific subset of molecules conserved in all multicellular organisms that converts a death inducing signal into intracellular biochemical processes, which ultimately lead to the complete destruction of the cell (Vaux and Korsmeyer 1999). Once triggered, apoptosis proceeds, with different kinetics depending on cell types, and culminates with cell disruption and formation of apoptotic bodies. A critical stage of apoptosis involves the acquisition of surface changes by dying cells that eventually results in the recognition and the uptake of these cells by phagocytes. Different changes on the surface of apoptotic cells such as the expression of thrombospondin binding sites, loss of sialic acid residues and exposure of phospholipids, like phosphatidylserine (PS), were previously described. Phospholipids are asymmetrically distributed between inner and outer leaflets of the plasma membrane, with phosphatidylcholine and sphingomyelin exposed on the external leaflet of the lipid bilayer and phosphatidylserine predominantly observed on the inner surface facing the cytosol. Cells undergoing apoptosis break up the phospholipid asymmetry of their plasma membrane and expose PS, which is translocated to the outer layer of the membrane. This occurs in the early phases of apoptotic cell death during which the cell membrane remains intact. PS exposure is, thus, an early and widespread hallmark of dying cells. Annexin V, belonging to a recently discovered family of proteins, the annexins, with anticoagulant properties, has proven to be a useful tool in detecting apoptotic cells, since it preferentially binds to negatively charged phospholipids, like PS, in the presence of $Ca^{2+}$ and shows minimal binding to phosphatidylcholine and sphingomyelin. Changes in PS asymmetry analyzed by measuring Annexin V binding to the cell membrane were detected before morphological changes associated with apoptosis occurred and before membrane integrity was lost.

By conjugating FITC to Annexin V it is possible to identify and quantify apoptotic cells on a single-cell basis by flow cytometry (Steensma et al., 2003). Simultaneous staining of cells with FITC-Annexin V (green fluorescence) and the non-vital dye propidium iodide (red fluorescence) allows (bivariant analysis) the discrimination of intact cells (FITC–PI–), early apoptotic (FITC+PI–) and late apoptotic or necrotic cells (FITC+PI+).

SUMMARY OF THE INVENTION

As mention in the background section, quality of a cryopreserved cell bank is critical in the use of a cell bank for the production of biopharmaceuticals. In the meaning of this invention, quality means, post thaw vitality, robustness, phenotypic/genetic stability, and long term preservation quality of cells, propagated and expanded starting from a cryopreserved cell bank. The present invention is based on the surprising observation that programmed cell death, particularly apoptosis, is the major cause of cell death after thawing of cryopreserved CHO cells of a frozen CHO cell bank. It also has been surprisingly demonstrated that the evidence of early apoptosis in cells of a culture propagated and expanded from a cryopreserved cell bank of CHO cells correlates with the quality of the CHO cell bank, which means with post-thaw vitality, robustness, phenotypic/genetic stability, and long term preservation quality, observed when cells are propagated and expanded starting from this cell bank. It has been furthermore demonstrated that Annexin V is a suitable marker to detect early apoptosis in CHO cells that have been thawed after cryopreservation.

The present invention therefore pertains to the use of Annexin V in characterizing a cryopreserved cell bank of CHO cells. Particularly, the present invention relates to the use of Annexin V in a process of characterizing a cryopreserved cell bank of CHO cells, preferably shortly after thawing a portion of cells of such a cell bank. According to a further embodiment of the present invention, said process includes the steps: a) thawing a portion of cells of a cryopreserved cell bank; b) cultivating said cells in a culture medium; c) incubating said cells with Annexin V; d) detecting cells and quantifying the number of cells that binds to Annexin V; e) detecting cells and quantifying the number of cells that do not bind to Annexin V; f) calculating the ratio of Annexin V-binding versus Annexin V-non-binding cells.

According to a further embodiment, the present invention also pertains to the use of Annexin V in a process of determining the quality of a CHO cell bank, wherein said process includes the steps: a) cryopreserving cells into parts in a liquid medium as a cell bank; b) thawing a portion of the cryopreserved cells of said cell bank; c) cultivating said cells in a culture medium; d) establishing the vitality-rate of said thawed cells by staining said cells with Annexin V. "Cryopreserving cells into parts" in a liquid medium means, that each about 0.25 to 3E7 cells are frozen in one to two ml of a liquid medium in a container. Per cell bank, about 200 containers or vials are frozen.

The present invention also pertains to the use of a Kit comprising Annexin V for the characterization of a cryopreserved cell bank of CHO cells post thawing, wherein Annexin V is used to determine the vitality-rate of the cryopreserved cells post thawing. According to a preferred embodiment of the present invention, the vitality-rate of cryopreserved cells post thawing is determined by a process including the steps a) thawing a portion of cells of a cryopreserved cell bank; b) cultivating said cells in a culture medium; c) incubating said cells with Annexin V; d) detecting cells and quantifying the number of cells that binds to Annexin V; e) detecting cells and quantifying the number of cells that do not bind to Annexin V; f) calculating the ratio of Annexin V-binding versus Annexin V-non-binding cells. Furthermore, the present invention also provides a Kit comprising Annexin V and a package leaflet including the information to use Annexin V in characterization of a cell bank of CHO cells by the inventive process, described herein.

The present invention further provides a process of characterizing a CHO cell bank including the steps a) thawing a portion of cells of a cryopreserved cell bank; b) cultivating said cells in an appropriate culture medium; c) incubating said cells with Annexin V; d) detecting cells and quantifying the number of cells that binds to Annexin V; e) detecting cells and quantifying the number of cells that do not bind to Annexin V; f) calculating the ratio of Annexin V-binding versus Annexin V-non-binding cells.

According to a further embodiment, the present invention also provides a process of measuring the vitality-rate of a CHO cell bank post-thawing, including the steps a) thawing a portion of cells of a cryopreserved cell bank b) cultivating said cells in an appropriate culture medium c) incubating said cells with Annexin V; d) detecting cells and quantifying the number of cells that binds to Annexin V; e) detecting cells and quantifying the number of cells that do not bind to Annexin V; f) calculating the ratio of Annexin V-binding versus Annexin V-non-binding cells.

BRIEF DESCRIPTION OF THE DRAWINGS

FIG. 1 shows a Fingerprint of cell death of CHO cell culture post cryopreservation. CHO DG44 cells were frozen using a freezing machine at a cell concentration of 2E7 cells/mL in 90% cultivation medium and 10% DMSO. Cells were analyzed by FACS at indicated timepoints. The first lane depicts forward scatter on the Y axis and side scatter on the X axis. Gates were set to distinguish cells that represent dead or living cells as judged by their morphology. Lane 2 shows the same graphs and Annexin V positive CHO cells are shown in white. Lane 3 depicts propidium iodide (PI) staining plotted versus Annexin V staining. Dots are grey according to the forward versus side scatter gating.

FIG. 4 shows use of early apoptosis measurements for testing of medium quality. CHO DG44 cells were frozen using a freezing machine at a cell conc. of 2E7 cells/mL in 90% cultivation medium and 10% DMSO. The size of the cell bank was 220 vials. Different media preparations were used for generation of three cell banks. Cultures were analyzed by FACS 6 h post thaw for cell cycle distribution, forward-side scatter, and Annexin V staining.

DETAILED DESCRIPTION OF THE INVENTION

The term "cell culture(s) was(were) initiated" refers to the time point, when cryopreserved cells are thawed and transferred to culture conditions suitable for the propagation and grown up of said cells to a cell culture.

The term "cell culture" means multiple cells cultivated in one container under conditions suitable for the growth of the cells.

The term "post thaw vitality" shall mean the time-course of post thaw recovery of cells propagated from a given cell bank measured in the percentage of viable cell to non-viable cells at the time of sub-cultivation. This parameter is essential for the time it takes to establish robust inoculum cultures and subsequent scale up for large scale cultivation. It therefore is a critical process parameter, The term "robustness" describes the reproducibility with which cell cultures recover after cryopreservation according to an established post thaw vitality pattern. A robust cell bank would result in minor differences amongst the post thaw performances of its different vials. The term "vial/vials" means a number of cells frozen in one container. Normally, a vial contains about 0.25 to 3E7 cells in one to two ml of a liquid medium.

The term "phenotypic/genetic stability" of cells is defined by the change in RNA and protein expression level observed when cells from a given cell bank are cultivated over a period of time relevant to the given process format, e.g., for about 100 to 300 sub-passages. A cell bank of poor quality, meaning low post-thaw vitalities could give rise to poor phenotypic/genetic stability due to a high selection pressure when cultures are initiated. A low post-thaw vitality in the meaning of the present invention means that not more than 50%, preferably not more than 30%, more preferably not more than 20%, and furthermore preferably not more than 15% of the cells are Annexin V positive within 6 h post thaw. In other words, a high quality cell bank is characterized in a vitality-rate post thawing of more than 50%, preferably more than 70%, more preferably more than 80%, and furthermore preferably more than 85%, which means Annexin V negative within 6 h post thaw.

The term "long term preservation quality" is defined by the change of the three above described parameters over a prolonged period of cryopreservation, for example about up to 20 years, of a given cell bank.

The necessity to remove serum from mammalian cell culture processes, particularly from culturing CHO cells, has resulted in higher sensitivity of cultures towards cell death at different stages of a production process. A detailed analysis of cell death during thawing of CHO cells subsequent to cryopreservation was provided. It was a surprisingly finding of the present invention that programmed cell death or apoptosis is the predominant form of cell death caused by cryopreservation of CHO cells. As early as 3 h hours after, an increased level of phosphatidylserine was surprisingly observed on the cell surface of CHO cells. Display of phosphatidylserine on the surface of CHO cells as a result from loss of phospholipids asymmetry is an early hallmark of programmed cell death. At this point, cellular membrane integrity is still intact.

Early time points after thaw, e.g., 3 h to 24 h post thawing, showed Annexin V positive stained CHO cells to still be morphologically intact (as seen in forward-side-scatter plots). At later time points (around 24-48 h post thaw), the majority of Annexin V positive stained CHO cells appeared to show signs of shrinking/membrane disassembly as seen by forward-side-scatter analysis. In accordance with these surprisingly findings, the percentage of CHO cells that could be stained with propidium iodide (PI) only increased significantly 24 h post thaw. These data describe for the first time nature and time course of cell death of CHO cells post cryopreservation. Certain CHO cells show signs of having initiated a destruction program within a few hours after being placed in warm culture medium and subsequently these cells disassemble over the period of 48 h.

Annexin V was initially described as a vascular protein with strong anticoagulant properties (Reutelsberger et al., 1985). It appears to belong to a multigene family of proteins defined by a repeated motif, originally termed the endonexin loop. In the meantime, gene sequences coding for the Annexin V protein of several species have been identified and cloned. For example, see NCBI Protein Data Base Accession No. NP_001145.

The present invention therefore relates to the use of Annexin V in characterizing a cryopreserved CHO cell bank. Particularly, the present invention relates to the use of Annexin V in a process of characterizing a cryopreserved cell bank of CHO cells. According to a further embodiment of the present invention, said process includes the steps: a) thawing a portion of cells of a cryopreserved cell bank; b) cultivating said cells in a culture medium; c) incubating said cells with Annexin V; d) detecting and quantifying the number of cells that binds to Annexin V; e) detecting cells and quantifying the number of cells that do not bind to Annexin V; and f) calculating the ratio of Annexin V-binding versus Annexin V-non-binding cells.

According to a further embodiment the present invention also pertains to the use of Annexin V in a process of determining the quality of a CHO cell bank, wherein said process includes the steps: a) cryopreserving cells into parts in a liquid medium as a cell bank; b) thawing a portion of the cryopreserved cells of said cell bank; c) cultivating said cells in a culture medium; and d) establishing the vitality-rate of said thawed cells by staining said cells with Annexin V. Criteria for the quality of a CHO cell bank are post-thaw vitality, robustness, phenotypic/genetic stability, and long term preservation quality, observed when cells are propagated and expanded starting from this cell bank. These criteria are mainly affected by the number of CHO cells which survive the freeze/thaw process, in other words the number of "intact cells." A high number of intact CHO cells guarantee a fast growth of the initial cell culture, reduce the number of sub-cultivation steps necessary to expand the cell culture up to the large fermentation scale and therefore to minimize the risk that genetic variants may be established and/or dominated the culture. The vitality-rate is preferably estimated by Annexin V staining, which means the detection and quantification of Annexin V-binding cells. Therefore, according to a more preferred embodiment of the present invention, the process of the Annexin V staining in order to estimate the vitality-rate of CHO cells propagated and expanded after thawing includes the steps: a) incubating the post-thawed cells with Annexin V; b) detecting cells and quantifying the number of cells that binds to Annexin V; c) detecting cells and quantifying the number of cells that do not bind to Annexin V; and d) calculating the ratio of Annexin V binding vs. Annexin V non-binding cells. Examples of CHO cells are given in Table 1.

TABLE 1

CHO cell lines

| CHO Cell line | Order Number |
| --- | --- |
| CHO | ECACC No. 8505302 |
| CHO-K1 | ATCC CCL-61 |
| CHO-DUKX | ATCC CRL-9096 |
| (=CHO duk-, CHO/dhfr-) | |
| CHO-DUKX B1 | ATCC CRL-9010 |
| CHO-DG44 | Urlaub et al., Cell 33[2], 405-412, 1983 |
| CHO Pro-5 | ATCC CRL-1781 |

A variety of assays for detection of apoptotic cell cultures has been described, including DNA-laddering and TUNEL assays (Gavrieli et al., et al., 1992; Wijsman et al., 1993). However, flow cytometric methods of apoptosis detection offer several advantages over the above techniques as they allow rapid quantification of properties of thousands of cells. The use of flow-cytometric measurements allow rapid high throughput evaluation of different strategies do generate a successful cell bank for a given cell line. For this reason and according to a further embodiment of the present invention, the Annexin V is labeled with fluorescein isothiocyanate (FITC). This allows the use of a flow-cytometric Annexin V affinity assays to estimate the vitality-rate of cells post thawing. Therefore, the present invention also pertains to a process of staining cryopreserved cells of a CHO cell bank post thawing a portion of cells of that cell bank with FITC-labeled Annexin V in a flow-cytometric assay. An example of such an assay is given herein more in detail in the section Examples.

The results provided herein gives an explanation for results typically seen when a freeze/thaw step is monitored by trypan blue exclusion analysis of cell viability (standard method which reflect the state of the art in characterization of cell banks). These classic thaw-control experiments generally show a high number of viable cells right after thaw and viability only decreases between 24 h and 48 h post thaw. A broad analysis of data obtained for CHO cell banks surprisingly revealed the predictive value of flow-cytometric Annexin V affinity assays. The percentage of apoptotic CHO cells measured as early as 6 h post thaw provides information on the success of a cryopreservation strategy that is usually only gained in classic thaw control experiments over a period of 2-10 days. The present invention therefore also provide the use of Annexin V in characterization of a CHO cell bank or in a process of determining the quality of a CHO cell bank, wherein the incubation step with Annexin V is performed within 24 h, preferably, 18 h, more preferred 12 h, further more preferred 9 h, further more preferred 6 h post-thaw and start of cultivation of the cryopreserved cells. In this connection use of flow-cytometric assay using FITC labeled Annexin V is the most preferred method.

According to a further embodiment, the present invention also pertains to the use of a Kit comprising Annexin V for the characterization of a cryopreserved CHO cell bank post thawing, wherein Annexin V is used to determine the vitality-rate of the cryopreserved CHO cells post thawing. According to a preferred embodiment of the present invention, the vitality-rate of a cell culture is determined by a process including the steps: a) thawing a portion of cells of a cryopreserved cell bank; b) cultivating said cells in a culture medium; c) incubating said cells with Annexin V; d) detecting cells and quantifying the number of cells that binds to Annexin V; e) detecting cells and quantifying the number of cells that do not bind to Annexin V; and f) calculating the ratio of Annexin V-binding vs. Annexin V-non-binding cells. Furthermore, the present invention also provides a Kit comprising Annexin V and a package leaflet including the information to use Annexin V in characterization of a CHO cell bank.

The present invention further provides a process of characterizing a CHO cell bank including the steps: a) thawing a portion of cells of a cryopreserved cell bank; b) cultivating said cells in an appropriate culture medium; c) incubating said cells with Annexin V; d) detecting cells and quantifying the number of cells that binds to Annexin V; e) detecting cells and quantifying the number of cells that do not bind to Annexin V; and f) calculating the ratio of Annexin V-binding versus Annexin V-non-binding cells. According to a further embodiment, the present invention also provides a process of measuring the vitality-rate of a CHO cell bank post-thaw, including the steps: a) thawing a portion of cells of a cryopreserved cell bank b) cultivating said cells in an appropriate culture medium c) incubating said cells with Annexin V; d) detecting cells and quantifying the number of cells that binds to Annexin V; e) detecting cells and quantifying the number of cells that do not bind to Annexin V; and f) calculating the ratio of Annexin V-binding vs. Annexin V-non-binding cells. As shown by the present invention, the percentage of apoptotic CHO cells measured as early as 24 to 6 h post thaw provides information on the success of a cryopreservation strategy for CHO cells that is usually only gained in classic thaw control experiments over a period of 2-10 days. The present invention therefore also provide the processes of characterizing a CHO cell bank or measuring the vitality-rate of a cell bank post-thaw, wherein the incubation step with Annexin V is performed within 6-24 hours post-thaw and start of cultivation of the cryopreserved cells.

CHO cells can be successfully stored in liquid nitrogen at around $-196°$ C. for prolonged periods of time. However, cells can usually not be frozen and thawed without the addition of cryoprotectants such as DMSO. Even then, the freeze-thaw process will result in the loss of cells. A critical parameter for the amount of this loss is the protocol used for the freeze and the thaw process. Generally it is beneficial to control the temperature decrease during freezing to ensure that the temperature drops at a rate to of around one degree per minute. To thaw CHO cells successfully it is required to warm the cryovial (thawed cells) as fast as possible to $37°$ C., the optimal cultivation temperature of almost all CHO cell lines. One way to ensure high recovery rates of cultures post thaw is to freeze cells in a medium containing high amounts of serum.

Recently, much work was focused on developing cryopreservation strategies for CHO cells without the use of serum in the freezing medium. A variety of cryoprotectants can facilitate successful long-term storage of cells without the presence of serum. In addition, the composition of the basal medium as such has a significant impact on the success of any cryopreservation. The described fast-track quality assessment of any such strategy will allow drastically reduced development times that are needed to generate reliable protocols for generation of a master or working cell bank for new CHO production cell lines. According to a further embodiment, the present invention also provides a process of analysing a culture medium for CHO cells with regard to the use of said medium for cryopreservation of CHO cells including the steps: a) cryopreserving CHO cells in a culture medium suitable for culturing those cells, preferably at temperatures below $-100°$ C., e.g., in fluid nitrogen, b) thawing a portion or all of the cryopreserved cells; c) cultivating said cells in an appropriate culture medium; d) incubating said cells with Annexin V; e) detecting cells and quantifying the number of cells that binds to Annexin V; f) detecting cells and quantifying the number of cells that do not bind to Annexin V; and g) calculating the ratio of Annexin V-binding versus Annexin V-non-binding cells.

Suitable culture media are those based on commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invtirogen), serum-free CHO Medium (Sigma), and protein-free CHO Medium (Sigma). According to a preferred process said medium includes specific crypro-tectants such as DMSO, BSA, methylcellulose, or glycine. According to a more preferred embodiment of this process, the incubation step with Annexin V is performed within 6-24 hours post-thaw and start of cultivation of the cryopreserved cells. Use of FITC-labeled Annexin V in flow-cytometric assay is a furthermore preferred embodiment of the inventive process.

The invention generally described above will be more readily understood by reference to the following examples, which are hereby included merely for the purpose of illustration of certain embodiments of the present invention and are not intended to limit the invention in any way.

Abbreviations:
BSA: bovine serum albumin
CHO: Chinese hamster ovary
DMSO: dimethyl sulfoxide
ELISA: enzyme-linked immunosorbant assay
FACS: fluorescence activated cell sorter
FITC: fluorescein isothiocyanate MCB: master cell bank
PBS: phosphate buffered saline
PCR: polymerase chain reaction
PI: propidium iodide
PPCB: post production cell bank
PS: phosphatidylserine
WCB: working cell bank Methods:

Cell Culture:

Cell banks of several CHO suspension cell lines used for production and development of biopharmaceuticals were investigated. All cell lines used are proprietary and their protein product may not be revealed. All cell lines used at production and development scale were maintained in serial seedstock cultures in surface-aerated T-Flasks (Nunc, Denmark) in incubators (Thermo, Germany) or sparged spinner flasks (Wheaton, USA) in specially designed incubator rooms at a temperature of 37° C. and an appropriate mixture of air and 5% $CO_2$. Seedstock cultures were split every 2-3 days with an appropriate splitting ratio and seed density. Cell concentration was determined in all cultures by using a hemocytometer. Viability was assessed by the trypan blue exclusion method. The cultures originated from master, working or safety cell banks and were thoroughly tested for sterility, mycoplasma, and the presence of adventitious agents. All operations took place in air-filtered laboratories and under strict procedures complying with "current Good Manufacturing Practices (cGMP). All culture media used are proprietary and their composition may not be revealed.

Cryopreservation:

Freezing and thawing were performed according to standard protocols and the fundamental law "freezing low-thawing fast." The cultures were taken in exponential phase from suspension cultures and were frozen in 1,8 mL plastic vials (Nunc, Demark) either by a computer-controlled freezing machine (Consarctic, Germany) with a specially designed freezing program or by a Styrofoam box in a −70° C. freezer. After freezing to −100° C. (freezing machine) or −70° C. (Styrofoam box) the cells were transferred to liquid nitrogen containers. Vials were stored in the gas phase of the liquid nitrogen (<−150° C.). The cell concentration in the freezing vials was 1-3E7 cells. DMSO (Merck, Germany) was used as a cryoprotectant at a concentration of 10%. The detailed freezing media used are also proprietary and their composition may not be revealed. CHO cells were thawed in an 37° C. water bath, diluted with appropriate medium, and centrifuged (Thermo, France) at 180×g.

Subsequently cells were seeded in cultivation medium with a defined cell concentration.

Flow Cytometry:

Green Annexin-V-FITC and red PI fluorescence were measured with a Coulter Epics XL flow cytometer (Coulter, Germany) using Expo32 software. Excitation was elicited at 488 nm with an Argon laser and measured using the standard band pass (530±20 nm) and long pass (>570 nm) filters. In each sample, 10000 events for apoptosis and 3000 events for cell cycle analysis were measured. Data were analyzed with the Expo32 analysis tool. To discriminate between dead and apoptotic cells, the membrane-impermeable DNA stain propidium iodide (PI) was added in parallel to Annexin V to the cell suspension. With this double staining it is possible to discriminate between vital, early-apoptotic, late-apoptotic, and necrotic cells. The Annexin V assay was performed according to the vendor's protocol (Becton-Dickinson, Germany). The cells were analyzed and apoptosis was quantified by flow cytometry. Propidium iodide staining was further used to determine cell cycle distribution. Samples were taken from cell suspensions without fixation. Cultures were centrifuged and washed with PBS (Gibco, Germany). Then, the PI staining solution (BioSure, USA) was added and incubation proceeded for 30 min. Subsequently, cells were analyzed by flow cytometry. The proportion of cells in each phase of the cell cycle was obtained through the Multicycle program (Phoenix Flow, USA).

Figure 1:
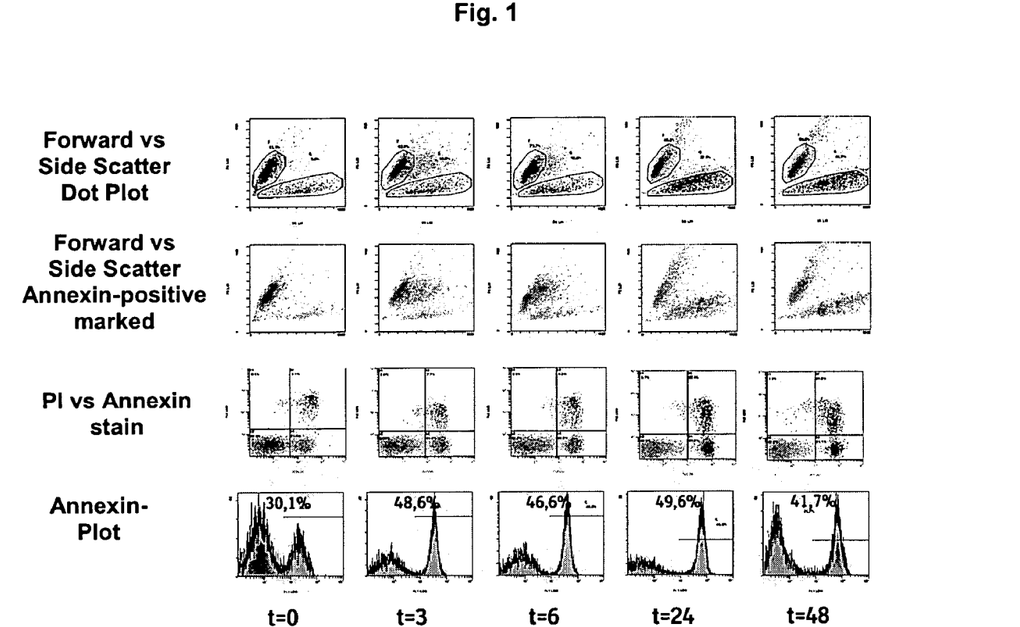

Results:

Quantitative analysis of cell death during the thaw of cryopreserved CHO cells:

Although it is known that CHO cells die when cultures of cells are reinitiated after cryopreservation the kinetic and nature of this cell death have not been described in great detail. To quantify the extent of programmed cell death in cell cultures of CHO cells during the first hours after thawing we determined the amount of phosphatidylserine displayed on the outer membrane of CHO cells. CHO DG44 cells and derivatives of this cell line are widely used for production of biopharmaceuticals. We first analyzed a cell bank of 220 vials generated for a CHO-derived production cell line. The cell bank was generated with a freezing medium free of animal components, such as serum, and was known to be particularly sensitive with regard to culture viability after thawing. Cells were analyzed by double staining with Annexin V and propidium iodide at time points 0 h, 3 h, 6 h, 24 h, and 48 h. A high percentage of approximately 30% Annexin V positive cells was detected right after cells were placed in cultivation medium (0 h), increasing to almost 50% within the first 3 h, and remaining at above 40% for the first 48 h post thaw. For all CHO DG44 cell banks analyzed so far, the peak level of Annexin V positive cells was reached between 3 h and 24 h post thaw. In contrast to that, the amount of PI positive cells remained relatively low immediately after thaw before it increased markedly 24 h post thaw. In the initial phase of apoptosis, PS is displayed on the cell surface and Annexin V binds it target. In this early phase, the plasma membrane is still able to exclude PI and, thus, cells are Annexin V+/PI− (FIG. 1, lower right quadrant). Subsequently, cells loose their plasma membrane integrity and their ability to exclude PI. These late apoptotic cells are Annexin V+/PI+ (FIG. 1, upper right quadrant). Therefore, these experiments demonstrate that the transition from early to late stage apoptosis only occurs after the first 6 hours post thaw. This is also seen in the forward-side scatter diagram (FIG. 1), showing an increase in very small cells, representing destructed cell bodies (FIG. 1) at the transition point around 24 hours post thaw.

Figure 2:
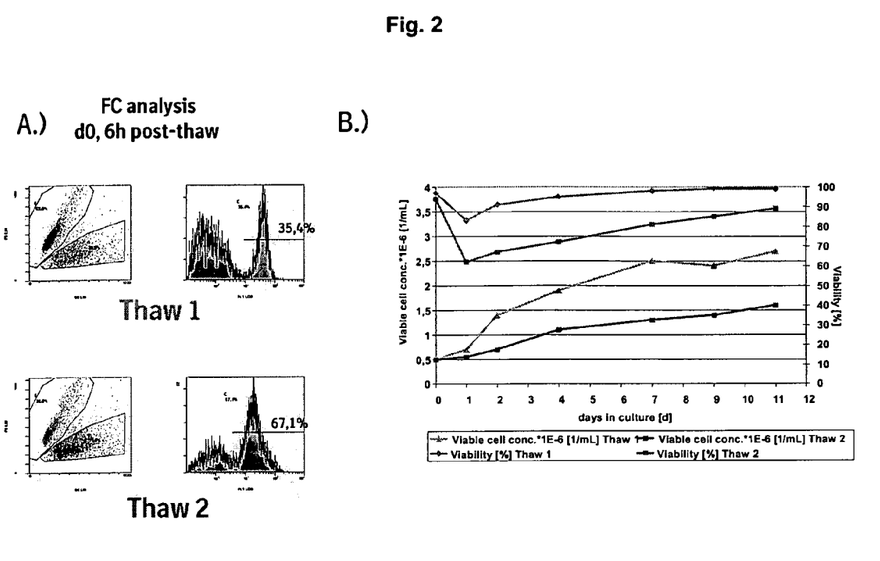
FIG. 2 shows 6 h post-thaw Annexin V staining predicts cell bank quality. A. CHO DG44 cells were frozen using a freezing machine at a cell concentration of 2E7 cells/mL in 90% cultivation medium and 10% DMSO. The size of the cell bank was 220 vials. A) FACS analysis of Annexin V stained cells 6 h post thaw. Data are plotted as forward side scatter graph (gates as described for FIG. 1) and as Annexin V intensity plot. B) Growth and viability of post-thaw cultures. Cells were counted for every passage. Simultaneously, viability was determined by trypan blue exclusion.

Post-thaw analysis by Annexin V staining serves as predictive early marker for CHO cell bank quality:

As quantification of apoptosis by Annexin V staining can be performed rapidly for a high number of samples it offers an attractive method for high-throughput analysis of different cryopreservation methods. We analyzed two CHO cell banks of two different CHO production cells by Annexin V staining and compared these data to trypan blue exclusion staining measured for six passages in culture (standard thaw control). As seen in FIG. 2A, the amount of phosphatidylserine-displaying cells varied significantly between cultures thawed from the two different cell banks (35% in thaw 1 versus 67% in thaw 2). The classic thawing control (FIG. 2B) showed the same significant difference between the culture viabilities from the different banks. Thaw 1 demonstrated a drop to 83% before the culture recovered to a viability of more than 90% four days post thaw. In contrast to that, only 60% of cells were viable 24 h after thaw 2. This culture took eleven days to reach 90% viability as determined by trypan blue exclusion. A cell bank of this quality would clearly not be suitable for a commercial production process. These data surprisingly demonstrate that the percentage of cells displaying PS on their surface predicts the outcome of classic thawing controls as early as 6 h post thaw.

Figure 3:
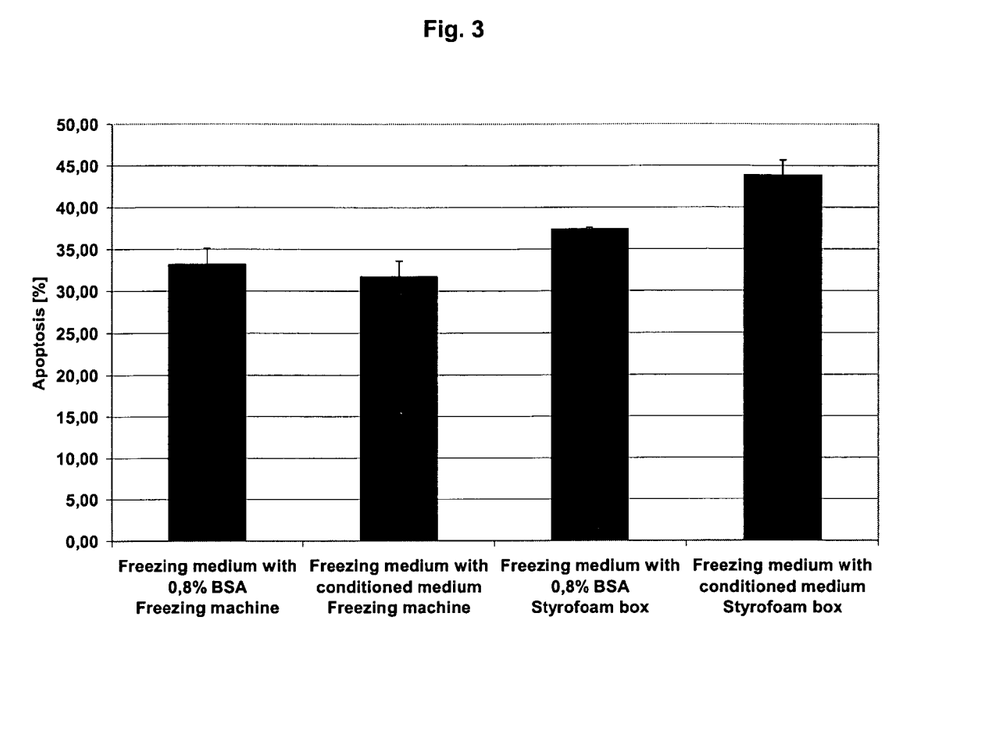
FIG. 3 shows different cell banks show different apoptosis after thaw. CHO DG44 was frozen using a freezing machine with a cell concentration of 1E7 or 2E7 cells/mL in different freezing media. The size of the cell banks was >200 vials. Cells were cryopreserved using a freezing machine or a polystyrene box in two different freezing media. Cultures were analyzed by Annexin V staining 6 h post thaw.

Cell bank quality can vary dramatically amongst different cell lines, cryopreservation protocols, and quality of cultivation medium:

To test the newly described method for cell bank quality assessment we analyzed a number of cell banks. Two CHO DG44 cell banks were generated, one containing 0.8% BSA in the freezing medium, the other containing a 50:50 mixture of conditioned and fresh medium without BSA. As depicted in FIG. 3, the cells showed significantly lower rates of early apoptosis for both freezing media. Furthermore, a beneficial effect of adding 0.8% BSA compared to storing cells in conditioned medium was only evident when styrofoam boxes were used.

Use of early post-thaw apoptosis measurements for fast-track development strategies:

As time to clinic and market supply is a crucial parameter for successful development of new biopharmaceuticals there is a growing interest in fast-track screening methods for process optimization and process improvements. We therefore determined the feasibility of using Annexin V measurements just 6 h post thaw to evaluate strategies for establishing successful cryopreservation of new CHO production cell lines.

Figure 4:
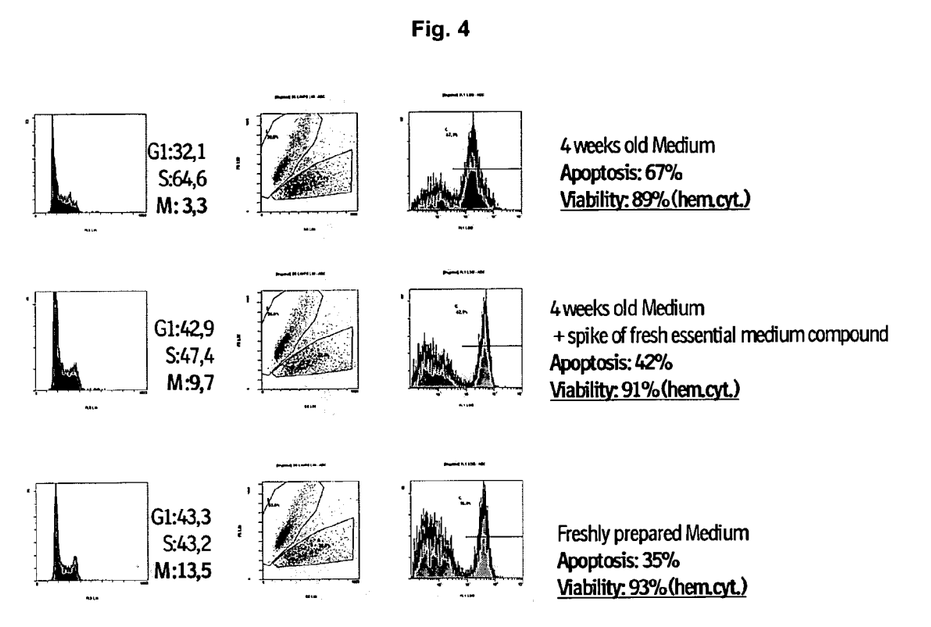

We surprisingly find out that early post-thaw apoptosis measurements are a sensitive tool for assessment of raw materials quality. An essential factor for successful cryopreservation of CHO cells is the quality of the medium used. Generally, GMP includes clearly defined expiry dates for use of media for culturing CHO cells. We investigated whether the harsh conditions of a freeze-thaw process may result in shorter timeframes for the use of media compared to standard cultivation procedures. We used a medium with a shelf life of four weeks for cultivation of CHO cells to investigate this further. FIG. 4 shows early apoptosis data (6 h post thaw) for CHO cells that were cryopreserved in freshly prepared medium (4 bottom), medium that was stored at 4 C. for four weeks (4 top) and medium that was stored at 4 C. for four weeks and was supplemented with a fresh preparation of an essential compound immediately before use (4 middle). These data show a decreased thaw performance for cells banks generated with this medium just before its expiration date. This effect could be reduced significantly by adding a newly prepared essential component of the relevant medium. Simultaneous determination of the cell cycle distribution 6 h post thaw showed that four week old medium had no growth inhibitory effect. These results surprisingly demonstrate how early post-thaw apoptosis measurements could be used for sensitive analyses of media and their components with regard to the use of media preparations for cryopreservation of CHO cells.

What is claimed is:

1. A method for characterizing a cryopreserved cell bank of CHO cells for Annexin V-binding, the method comprising:
    a. thawing a portion of cells of said cryopreserved cell bank of CHO cells;
    b. cultivating said cells in a culture medium;
    c. incubating said cells with Annexin V;
    d. detecting cells and quantifying the number of thawed CHO cells that bind to Annexin V;
    e. detecting cells and quantifying the number of thawed CHO cells that do not bind to Annexin V; and
    f. calculating the ratio of Annexin V-binding thawed CHO cells vs. Annexin V-non-binding thawed CHO cells; wherein
        the step of incubating said cells with Annexin V is carried out within 24 hours post-thaw.

2. The method of claim 1, wherein Annexin V is incubated with the thawed CHO cells within 6 hours post-thaw.

3. The method of claim 1, wherein the Annexin V is labeled with fluorescein isothiocyanate (FITC).

4. The method of claim 1, wherein the cryopreserved cell bank of CHO cells comprises CHO cells that are cryopreserved into parts in a liquid medium.

5. The method of claim 1, wherein the thawed CHO cells are thawed from a portion of the cryopreserved cell bank.

* * * * *